(12) United States Patent
Henry, Jr.

(10) Patent No.: US 10,568,359 B2
(45) Date of Patent: Feb. 25, 2020

(54) SENSOR FOR AN AEROSOL DELIVERY DEVICE

(71) Applicant: RAI Strategic Holdings, Inc., Winston-Salem, NC (US)

(72) Inventor: Raymond Charles Henry, Jr., Cary, NC (US)

(73) Assignee: RAI Strategic Holdings, Inc., Winston-Salem, NC (US)

(*) Notice: Subject to any disclaimer, the term of this patent is extended or adjusted under 35 U.S.C. 154(b) by 12 days.

(21) Appl. No.: 15/850,264

(22) Filed: Dec. 21, 2017

(65) Prior Publication Data

US 2018/0132536 A1    May 17, 2018

Related U.S. Application Data

(62) Division of application No. 14/245,105, filed on Apr. 4, 2014, now Pat. No. 9,877,510.

(51) Int. Cl.
*A24F 47/00* (2006.01)
*A61M 15/06* (2006.01)
*G01F 1/28* (2006.01)

(52) U.S. Cl.
CPC .......... *A24F 47/008* (2013.01); *A61M 15/06* (2013.01); *G01F 1/28* (2013.01); *A61M 2205/3334* (2013.01)

(58) Field of Classification Search
CPC .................................................. A24F 47/008
See application file for complete search history.

(56) References Cited

U.S. PATENT DOCUMENTS 1,771,366 A    7/1930    Wyss et al.
2,057,353 A    10/1936   Whittemore, Jr.
(Continued)

FOREIGN PATENT DOCUMENTS

AU    276250    7/1965
CA    2 641 869    5/2010
(Continued)

OTHER PUBLICATIONS

Mechatronics, What is Schmitt trigger?, downloaded on Oct. 24, 2018, How to Mechatronics [downloaded from howtomechatronics.com].*

(Continued)

*Primary Examiner* — Anthony Calandra
(74) *Attorney, Agent, or Firm* — Womble Bond Dickinson (US) LLP

(57) ABSTRACT

The present disclosure relates to an aerosol delivery device including a variable output flow sensor. The variable output flow sensor particularly can be a flex/bend sensor wherein output from the sensor varies based upon changes in electrical current flow (e.g., resistance) along an extension of the sensor relative to flexing or bending of the extension resulting from airflow across the extension. The disclosure further provides methods for controlling operation of an aerosol delivery device through utilization of a variable output flow sensor. In particular, control of functional elements (e.g., a heating member, a fluid delivery member, and a sensory feedback member) can allow for real-time changes in the operation of the aerosol delivery device relative to airflow through the device.

7 Claims, 7 Drawing Sheets

(56) References Cited

U.S. PATENT DOCUMENTS

| | | |
|---|---|---|
| 2,104,266 A | 1/1938 | McCormick |
| 2,805,669 A | 9/1957 | Meriro |
| 3,200,819 A | 4/1963 | Gilbert |
| 3,398,754 A | 6/1966 | Tughan |
| 3,316,919 A | 5/1967 | Green et al. |
| 3,419,015 A | 12/1968 | Wochnowski |
| 3,424,171 A | 1/1969 | Rooker |
| 3,476,118 A | 11/1969 | Luttich |
| 4,054,145 A | 10/1977 | Berndt et al. |
| 4,131,117 A | 12/1978 | Kite et al. |
| 4,150,677 A | 4/1979 | Osborne |
| 4,190,046 A | 2/1980 | Virag |
| 4,219,032 A | 8/1980 | Tabatznik et al. |
| 4,259,970 A | 4/1981 | Green, Jr. |
| 4,284,089 A | 8/1981 | Ray |
| 4,303,083 A | 12/1981 | Burruss, Jr. |
| 4,449,541 A | 5/1984 | Mays et al. |
| 4,506,682 A | 3/1985 | Muller |
| 4,635,651 A | 1/1987 | Jacobs |
| 4,674,519 A | 6/1987 | Keritsis et al. |
| 4,708,151 A | 11/1987 | Shelar |
| 4,714,082 A | 12/1987 | Banerjee et al. |
| 4,735,217 A | 4/1988 | Gerth et al. |
| 4,756,318 A | 7/1988 | Clearman et al. |
| 4,771,795 A | 9/1988 | White et al. |
| 4,776,353 A | 10/1988 | Lilja et al. |
| 4,793,365 A | 12/1988 | Sensabaugh, Jr. et al. |
| 4,800,903 A | 1/1989 | Ray et al. |
| 4,819,665 A | 4/1989 | Roberts et al. |
| 4,821,749 A | 4/1989 | Toft et al. |
| 4,830,028 A | 5/1989 | Lawson et al. |
| 4,836,224 A | 6/1989 | Lawson et al. |
| 4,836,225 A | 6/1989 | Sudoh |
| 4,848,374 A | 7/1989 | Chard et al. |
| 4,848,376 A | 7/1989 | Lilja et al. |
| 4,874,000 A | 10/1989 | Tamol et al. |
| 4,880,018 A | 11/1989 | Graves, Jr. et al. |
| 4,887,619 A | 12/1989 | Burcham, Jr. et al. |
| 4,907,606 A | 3/1990 | Lilja et al. |
| 4,913,168 A | 4/1990 | Potter et al. |
| 4,917,119 A | 4/1990 | Potter et al. |
| 4,917,128 A | 4/1990 | Clearman et al. |
| 4,922,901 A | 5/1990 | Brooks et al. |
| 4,924,888 A | 5/1990 | Perfetti et al. |
| 4,928,714 A | 5/1990 | Shannon |
| 4,938,236 A | 7/1990 | Banerjee et al. |
| 4,941,483 A | 7/1990 | Ridings et al. |
| 4,941,484 A | 7/1990 | Clapp et al. |
| 4,945,931 A | 8/1990 | Gori |
| 4,947,874 A | 8/1990 | Brooks et al. |
| 4,947,875 A | 8/1990 | Brooks et al. |
| 4,972,854 A | 11/1990 | Kiernan et al. |
| 4,972,855 A | 11/1990 | Kuriyama et al. |
| 4,986,286 A | 1/1991 | Roberts et al. |
| 4,987,906 A | 1/1991 | Young et al. |
| 5,005,593 A | 4/1991 | Fagg |
| 5,019,122 A | 5/1991 | Clearman et al. |
| 5,022,416 A | 6/1991 | Watson |
| 5,042,510 A | 8/1991 | Curtiss et al. |
| 5,056,537 A | 10/1991 | Brown et al. |
| 5,060,669 A | 10/1991 | White et al. |
| 5,060,671 A | 10/1991 | Counts et al. |
| 5,065,775 A | 11/1991 | Fagg |
| 5,072,744 A | 12/1991 | Luke et al. |
| 5,074,319 A | 12/1991 | White et al. |
| 5,076,296 A | 12/1991 | Nystrom et al. |
| 5,086,705 A | 2/1992 | Jarvis |
| 5,093,894 A | 3/1992 | Deevi et al. |
| 5,095,921 A | 3/1992 | Losee et al. |
| 5,097,850 A | 3/1992 | Braunshteyn et al. |
| 5,099,862 A | 3/1992 | White et al. |
| 5,099,864 A | 3/1992 | Young et al. |
| 5,103,842 A | 4/1992 | Strang et al. |
| 5,121,757 A | 6/1992 | White et al. |
| 5,129,409 A | 7/1992 | White et al. |
| 5,131,415 A | 7/1992 | Munoz et al. |
| 5,144,962 A | 8/1992 | Counts et al. |
| 5,143,097 A | 9/1992 | Sohn et al. |
| 5,146,934 A | 9/1992 | Deevi et al. |
| 5,159,940 A | 11/1992 | Hayward et al. |
| 5,159,942 A | 11/1992 | Brinkley et al. |
| 5,179,966 A | 1/1993 | Losee et al. |
| 5,211,684 A | 5/1993 | Shannon et al. |
| 5,220,930 A | 6/1993 | Gentry |
| 5,224,498 A | 7/1993 | Deevi et al. |
| 5,228,460 A | 7/1993 | Sprinkel, Jr. et al. |
| 5,230,354 A | 7/1993 | Smith et al. |
| 5,235,992 A | 8/1993 | Sensabaugh |
| 5,243,999 A | 9/1993 | Smith |
| 5,246,018 A | 9/1993 | Deevi et al. |
| 5,249,586 A | 10/1993 | Morgan et al. |
| 5,261,424 A | 11/1993 | Sprinkel, Jr. |
| 5,269,327 A | 12/1993 | Counts et al. |
| 5,285,798 A | 2/1994 | Banerjee et al. |
| 5,293,883 A | 3/1994 | Edwards |
| 5,301,694 A | 4/1994 | Raymond |
| 5,303,720 A | 4/1994 | Banerjee et al. |
| 5,318,050 A | 6/1994 | Gonzalez-Parra et al. |
| 5,322,075 A | 6/1994 | Deevi et al. |
| 5,322,076 A | 6/1994 | Brinkley et al. |
| 5,339,838 A | 8/1994 | Young et al. |
| 5,345,951 A | 9/1994 | Serrano et al. |
| 5,353,813 A | 10/1994 | Deevi et al. |
| 5,357,984 A | 10/1994 | Farrier et al. |
| 5,360,023 A | 11/1994 | Blakley et al. |
| 5,369,723 A | 11/1994 | Counts et al. |
| 5,372,148 A | 12/1994 | McCafferty et al. |
| 5,377,698 A | 1/1995 | Litzinger et al. |
| 5,388,574 A | 2/1995 | Ingebrethsen et al. |
| 5,388,594 A | 2/1995 | Counts et al. |
| 5,408,574 A | 4/1995 | Deevi et al. |
| 5,411,789 A | 5/1995 | Margolin |
| 5,435,325 A | 7/1995 | Clapp et al. |
| 5,445,169 A | 8/1995 | Brinkley et al. |
| 5,468,266 A | 11/1995 | Bensalem et al. |
| 5,468,936 A | 11/1995 | Deevi et al. |
| 5,479,948 A | 1/1996 | Counts et al. |
| 5,498,850 A | 3/1996 | Das |
| 5,498,855 A | 3/1996 | Deevi et al. |
| 5,499,636 A | 3/1996 | Baggett, Jr. et al. |
| 5,501,237 A | 3/1996 | Young et al. |
| 5,505,214 A | 4/1996 | Collins et al. |
| 5,515,842 A | 5/1996 | Ramseyer et al. |
| 5,530,225 A | 6/1996 | Hajaligol |
| 5,551,450 A | 9/1996 | Hemsley |
| 5,551,451 A | 9/1996 | Riggs et al. |
| 5,564,442 A | 10/1996 | MacDonald et al. |
| 5,573,692 A | 11/1996 | Das et al. |
| 5,591,368 A | 1/1997 | Fleischhauer et al. |
| 5,593,792 A | 1/1997 | Farrier et al. |
| 5,595,577 A | 1/1997 | Bensalem et al. |
| 5,596,706 A | 1/1997 | Sikk et al. |
| 5,611,360 A | 3/1997 | Tang |
| 5,613,504 A | 3/1997 | Collins et al. |
| 5,613,505 A | 3/1997 | Campbell et al. |
| 5,649,552 A | 7/1997 | Cho et al. |
| 5,649,554 A | 7/1997 | Sprinkel et al. |
| 5,659,656 A | 8/1997 | Das |
| 5,665,262 A | 9/1997 | Hajaligol et al. |
| 5,666,976 A | 9/1997 | Adams et al. |
| 5,666,977 A | 9/1997 | Higgins et al. |
| 5,666,978 A | 9/1997 | Counts et al. |
| 5,687,746 A | 11/1997 | Rose et al. |
| 5,692,525 A | 12/1997 | Counts et al. |
| 5,692,526 A | 12/1997 | Adams et al. |
| 5,708,258 A | 1/1998 | Counts et al. |
| 5,711,320 A | 1/1998 | Martin |
| 5,726,421 A | 3/1998 | Fleischhauer et al. |
| 5,727,571 A | 3/1998 | Meiring et al. |
| 5,730,158 A | 3/1998 | Collins et al. |
| 5,750,964 A | 5/1998 | Counts et al. |
| 5,799,663 A | 9/1998 | Gross et al. |
| 5,816,263 A | 10/1998 | Counts et al. |
| 5,819,756 A | 10/1998 | Mielordt |

(56) References Cited

U.S. PATENT DOCUMENTS

| | | |
|---|---|---|
| 5,829,453 A | 11/1998 | White et al. |
| 5,865,185 A | 2/1999 | Collins et al. |
| 5,865,186 A | 2/1999 | Volsey, II |
| 5,878,752 A | 3/1999 | Adams et al. |
| 5,880,439 A | 3/1999 | Deevi et al. |
| 5,894,841 A | 4/1999 | Voges |
| 5,915,387 A | 7/1999 | Baggett, Jr. et al. |
| 5,934,289 A | 8/1999 | Watkins et al. |
| 5,954,979 A | 9/1999 | Counts et al. |
| 5,967,148 A | 10/1999 | Harris et al. |
| 6,026,820 A | 2/2000 | Baggett, Jr. et al. |
| 6,033,623 A | 3/2000 | Deevi et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,116,247 A | 9/2000 | Banyasz et al. |
| 6,119,700 A | 9/2000 | Fleischhauer et al. |
| 6,125,853 A | 10/2000 | Susa et al. |
| 6,125,855 A | 10/2000 | Nevett et al. |
| 6,125,866 A | 10/2000 | Nichols et al. |
| 6,155,268 A | 12/2000 | Takeuchi |
| 6,164,287 A | 12/2000 | White |
| 6,182,670 B1 | 2/2001 | White |
| 6,196,218 B1 | 3/2001 | Voges |
| 6,196,219 B1 | 3/2001 | Hess et al. |
| 6,216,706 B1 | 4/2001 | Kumar et al. |
| 6,289,898 B1 | 9/2001 | Fournier et al. |
| 6,349,729 B1 | 2/2002 | Pham |
| 6,357,671 B1 | 3/2002 | Cewers |
| 6,418,938 B1 | 7/2002 | Fleischhauer et al. |
| 6,446,426 B1 | 8/2002 | Sweeney et al. |
| 6,532,965 B1 | 3/2003 | Abhulimen et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,701,936 B2 | 3/2004 | Shafer et al. |
| 6,715,494 B1 | 4/2004 | McCoy |
| 6,730,832 B1 | 5/2004 | Dominguez et al. |
| 6,772,756 B2 | 8/2004 | Shayan |
| 6,803,545 B2 | 10/2004 | Blake et al. |
| 6,803,550 B2 | 10/2004 | Sharpe et al. |
| 6,810,883 B2 | 11/2004 | Felter et al. |
| 6,854,461 B2 | 2/2005 | Nichols |
| 6,854,470 B1 | 2/2005 | Pu |
| 6,994,096 B2 | 2/2006 | Rostami et al. |
| 7,011,096 B2 | 3/2006 | Li et al. |
| 7,017,585 B2 | 3/2006 | Li et al. |
| 7,025,066 B2 | 4/2006 | Lawson et al. |
| 7,117,867 B2 | 10/2006 | Cox et al. |
| 7,163,015 B2 | 1/2007 | Moffitt |
| 7,173,322 B2 | 2/2007 | Cox et al. |
| 7,185,659 B2 | 3/2007 | Sharpe et al. |
| 7,234,470 B2 | 6/2007 | Yang |
| 7,290,549 B2 | 11/2007 | Banerjee et al. |
| 7,293,565 B2 | 11/2007 | Griffin et al. |
| 7,392,809 B2 | 7/2008 | Larson et al. |
| 7,513,253 B2 | 4/2009 | Kobayashi et al. |
| 7,647,932 B2 | 1/2010 | Cantrell et al. |
| 7,690,385 B2 | 4/2010 | Moffitt |
| 7,692,123 B2 | 4/2010 | Baba et al. |
| 7,726,320 B2 | 6/2010 | Robinson et al. |
| 7,775,459 B2 | 8/2010 | Martens, III et al. |
| 7,810,505 B2 | 10/2010 | Yang |
| 7,832,410 B2 | 11/2010 | Hon |
| 7,845,359 B2 | 12/2010 | Montaser |
| 7,878,209 B2 | 2/2011 | Newbery et al. |
| 7,896,006 B2 | 3/2011 | Hamano et al. |
| 8,066,010 B2 | 11/2011 | Newbery et al. |
| 8,079,371 B2 | 12/2011 | Robinson et al. |
| 8,127,772 B2 | 3/2012 | Montaser |
| 8,156,944 B2 | 4/2012 | Han |
| 8,365,742 B2 | 2/2013 | Hon |
| 8,375,957 B2 | 2/2013 | Hon |
| 8,393,331 B2 | 3/2013 | Hon |
| 8,479,583 B1 | 7/2013 | LaComb et al. |
| 2002/0146242 A1 | 10/2002 | Vieira |
| 2003/0131859 A1 | 7/2003 | Li et al. |
| 2003/0226837 A1 | 12/2003 | Blake et al. |
| 2004/0020500 A1 | 2/2004 | Wrenn et al. |
| 2004/0118401 A1 | 6/2004 | Smith et al. |
| 2004/0129280 A1 | 7/2004 | Woodson et al. |
| 2004/0149296 A1 | 8/2004 | Rostami et al. |
| 2004/0200488 A1 | 10/2004 | Felter et al. |
| 2004/0224435 A1 | 11/2004 | Shibata et al. |
| 2004/0226568 A1 | 11/2004 | Takeuchi et al. |
| 2004/0255965 A1 | 12/2004 | Perfetti et al. |
| 2005/0016549 A1 | 1/2005 | Banerjee et al. |
| 2005/0016550 A1 | 1/2005 | Katase |
| 2005/0066986 A1 | 3/2005 | Nestor et al. |
| 2005/0151126 A1 | 7/2005 | Yamakawa et al. |
| 2005/0155602 A1 | 7/2005 | Lipp |
| 2005/0172976 A1 | 8/2005 | Newman et al. |
| 2005/0274390 A1 | 12/2005 | Banerjee et al. |
| 2006/0016453 A1 | 1/2006 | Kim |
| 2006/0032501 A1 | 2/2006 | Hale et al. |
| 2006/0070633 A1 | 4/2006 | Rostami et al. |
| 2006/0162733 A1 | 7/2006 | McGrath et al. |
| 2006/0185687 A1 | 8/2006 | Hearn et al. |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2007/0283972 A1 | 12/2007 | Monsees et al. |
| 2008/0085103 A1 | 4/2008 | Beland et al. |
| 2008/0092912 A1 | 4/2008 | Robinson et al. |
| 2008/0149118 A1 | 6/2008 | Oglesby et al. |
| 2008/0245377 A1 | 10/2008 | Marshall et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0065010 A1 | 3/2009 | Shands |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0260641 A1 | 10/2009 | Monsees et al. |
| 2009/0260642 A1 | 10/2009 | Monsees et al. |
| 2009/0272379 A1 | 11/2009 | Thorens et al. |
| 2009/0283103 A1 | 11/2009 | Nielsen et al. |
| 2009/0293892 A1 | 12/2009 | Williams et al. |
| 2009/0320863 A1 | 12/2009 | Fernando et al. |
| 2009/0324206 A1 | 12/2009 | Young et al. |
| 2010/0006113 A1 | 1/2010 | Urtsev et al. |
| 2010/0024834 A1 | 2/2010 | Oglesby et al. |
| 2010/0043809 A1 | 2/2010 | Magnon |
| 2010/0059070 A1 | 3/2010 | Potter et al. |
| 2010/0059073 A1 | 3/2010 | Hoffmann et al. |
| 2010/0065075 A1 | 3/2010 | Banerjee et al. |
| 2010/0083959 A1 | 4/2010 | Siller |
| 2010/0163063 A1 | 7/2010 | Fernando et al. |
| 2010/0200006 A1 | 8/2010 | Robinson et al. |
| 2010/0229881 A1 | 9/2010 | Hearn |
| 2010/0242974 A1 | 9/2010 | Pan |
| 2010/0242976 A1 | 9/2010 | Katayama et al. |
| 2010/0258139 A1 | 10/2010 | Onishi et al. |
| 2010/0300467 A1 | 12/2010 | Kuistilla et al. |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0073121 A1 | 3/2011 | Levin et al. |
| 2011/0088707 A1 | 4/2011 | Hajaligol |
| 2011/0094523 A1 | 4/2011 | Thorens et al. |
| 2011/0120480 A1 | 5/2011 | Brenneise |
| 2011/0126847 A1 | 6/2011 | Zuber et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0162663 A1 | 7/2011 | Bryman |

(56) References Cited

U.S. PATENT DOCUMENTS

| | | |
|---|---|---|
| 2011/0168194 A1 | 7/2011 | Hon |
| 2011/0180082 A1 | 7/2011 | Banerjee et al. |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0048266 A1 | 3/2012 | Alelov |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0186594 A1 | 7/2012 | Liu |
| 2012/0231464 A1 | 9/2012 | Yu et al. |
| 2012/0279512 A1 | 11/2012 | Hon |
| 2012/0318882 A1 | 12/2012 | Abehasera |
| 2013/0081625 A1 | 4/2013 | Rustad et al. |
| 2013/0081642 A1 | 4/2013 | Safari |
| 2013/0298905 A1 | 11/2013 | Levin et al. |
| 2013/0306084 A1 | 11/2013 | Flick |
| 2013/0319439 A1 | 12/2013 | Gorelick et al. |
| 2013/0333712 A1 * | 12/2013 | Scatterday ............ A61M 15/06 131/329 |
| 2013/0340750 A1 | 12/2013 | Thorens et al. |
| 2013/0340775 A1 | 12/2013 | Juster et al. |
| 2015/0000684 A1 | 1/2015 | Wu et al. |
| 2015/0068523 A1 | 3/2015 | Powers et al. |
| 2015/0257445 A1 | 9/2015 | Henry, Jr. et al. |
| 2015/0366266 A1 | 12/2015 | Chen et al. |

FOREIGN PATENT DOCUMENTS

| | | |
|---|---|---|
| CA | 2 752 255 | 8/2010 |
| CN | 1069198 | 2/1993 |
| CN | 1541577 | 11/2004 |
| CN | 1657111 | 8/2005 |
| CN | 2719043 | 8/2005 |
| CN | 1925886 | 3/2007 |
| CN | 200997909 | 1/2008 |
| CN | 101116542 | 2/2008 |
| CN | 101176805 | 5/2008 |
| CN | 101527187 | 9/2009 |
| CN | 201379072 | 1/2010 |
| DE | 10 2006 004 484 | 8/2007 |
| DE | 102006041042 | 3/2008 |
| DE | 20 2009 010 4 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| EP | 2 468 118 | 6/2012 |
| GB | 1444461 | 7/1976 |
| GB | 1 520 432 | 8/1978 |
| GB | 2469850 | 11/2010 |
| WO | WO 1986/02528 | 5/1986 |
| WO | WO 1997/48293 | 12/1997 |
| WO | WO 02/37990 | 5/2002 |
| WO | WO 2004/043175 | 5/2004 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/091593 | 8/2010 |
| WO | WO 2010/118644 | 10/2010 |
| WO | WO 2010/140937 | 12/2010 |
| WO | WO-2010145805 A1 * | 12/2010 ............ A24F 47/008 |
| WO | WO 2011/010334 | 1/2011 |
| WO | WO 2011/081558 | 7/2011 |
| WO | WO 2012/072762 | 6/2012 |
| WO | WO 2012/100523 | 8/2012 |
| WO | WO 2013/089551 | 6/2013 |

OTHER PUBLICATIONS

Electronics-tutorials-.ws, Capacitive Reactance, downloaded online Jun. 25, 2017.

* cited by examiner

SENSOR FOR AN AEROSOL DELIVERY DEVICE

CROSS-REFERENCE TO RELATED APPLICATIONS

The present application is a divisional of U.S. application Ser. No. 14/245,105 filed Apr. 4, 2014, the disclosure of which is incorporated by reference herein in its entirety.

FIELD OF THE DISCLOSURE

The present disclosure relates to aerosol delivery devices such as smoking articles. The aerosol delivery device may be configured to heat a material, which may be made or derived from tobacco or otherwise incorporate tobacco, to form an inhalable substance for human consumption. The aerosol delivery device particularly can incorporate a variable output sensor.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. Pub. No. 2013/0255702 to Griffith Jr. et al., U.S. Pat. Pub. No. 2014/0000638 to Sebastian et al., U.S. patent application Ser. No. 13/602,871 to Collett et al., filed Sep. 4, 2012, U.S. patent application Ser. No. 13/647,000 to Sears et al., filed Oct. 8, 2012, U.S. patent application Ser. No. 13/826,929 to Ampolini et al., filed Mar. 14, 2013, and U.S. patent application Ser. No. 14/011,992 to Davis et al., filed Aug. 28, 2013, which are incorporated herein by reference in their entirety.

It would be desirable to provide a smoking article that employs heat produced by electrical energy to provide the sensations of cigarette, cigar, or pipe smoking, that does so without combusting or pyrolyzing tobacco to any significant degree, that does so without the need of a combustion heat source, and that does so without necessarily delivering considerable quantities of incomplete combustion and pyrolysis products. Further, advances with respect to manufacturing electronic smoking articles would be desirable.

SUMMARY OF THE DISCLOSURE

The present disclosure relates to materials and combinations thereof useful in aerosol delivery devices, such as electronic smoking articles and like personal devices. In particular, the present disclosure relates to an aerosol delivery device that includes a sensor that is configured to detect airflow through at least a portion of the device and to particularly detect one or more properties of the airflow, such an airflow rate or volume.

In some embodiments, a sensor useful according to the present disclosure can be a flex/bend sensor. For example, a flex/bend sensor can comprise an electrical connection and an extension. The extension can be configured for angular displacement, such as when subjected to an airflow, particularly an airflow that is not substantially parallel to an axis along the length of the extension. Such angular displacement of the extension of the bend/flex sensor (or other analog measurement devices adapted for output of a continuous detection signal) can form the basis for a variable signal output that can vary across a continuous range based upon a property of the airflow. The variable signal output by the sensor can be interpreted by a controller, such as microprocessor, and form the basis for control of the operation of one or more functional elements of the aerosol delivery device, such as a heating member, a fluid delivery member, or a sensory feedback member.

Although known aerosol delivery devices may include a sensor for detecting draw on the device, such known sensors are configured to provide a "trigger" signal that is generated upon reaching a threshold and that does not provide a variable output. For example, an electret microphone is known to be used as a sensor in an aerosol delivery device, and such sensor uses a diaphragm that moves in response to a differential pressure that arises when a user draws (i.e., takes a "puff") on the aerosol delivery device. The sensor is designed so that no signal is formed until the draw on the device is sufficient to cause a pressure differential that is sufficiently large to displace the diaphragm. When the diaphragm moves, a small charge is generated which functions as the trigger signal to activate the device—e.g., cause power delivery from a battery to a heating element. While such sensor may be suitable to detect the presence of airflow at a threshold and output an on/off signal similar to a switch, such sensor cannot provide indication of any particular properties of the airflow, such as strength of the airflow, more particularly the airflow rate, volume, or the like.

A sensor utilized in an aerosol delivery device according to the present disclosure, however, can be configured to detect specific properties of the airflow through an aerosol delivery device and output a signal across a continuous range that varies in relation to the property of the airflow measured. For example, the output signal can relate information regarding the rate of airflow, which may correspond to the intensity of the draw on the device by a user, and the device can include control elements configured to utilize the output signal from the sensor to active the heater in a defined manner relative to the output signal. In other words, in some embodiments, as airflow rate through the aerosol delivery device increases, the electrical current delivered to a heating member may increase and thus increase heating by the heating member. Similar relative changes in operation may be controlled in relation to one or more further functional elements of the aerosol delivery device. In this manner, an aerosol delivery device may be configured to provide for adaptive functioning and thus improve output consistency of the device or otherwise improve a user experience with the device.

In some embodiments, the present disclosure provides an aerosol delivery device comprising: a housing; a sensor within the housing configured to detect an airflow through at least a portion of the housing and output a variable signal that varies based upon one or more properties of the airflow; and a controller configured to receive the variable signal from the sensor and control the operation of at least one functional element of the device based on the variable signal from the sensor. Specifically, the sensor can be flex/bend sensor, and such flex/bend sensor can comprise an electrical connection and an extension. The variable signal output by the sensor can correspond to an angular displacement of the extension, such as a change in the bend radius of the extension of the sensor.

The aerosol delivery device further can comprise an electronic circuit board, and the electrical connection of the sensor can be attached to the electronic circuit board. In some embodiments, the electronic circuit board can comprise an aperture positionally aligned with the extension and the airflow through the housing. Similarly, the housing can define a flow channel configured to receive airflow therethrough, and at least a portion of the extension of the sensor can be positioned in the flow channel.

In some embodiments, a longitudinal length of the extension can be oriented in a non-parallel direction relative to a longitudinal length of the housing. In further embodiments, a longitudinal length of the extension can be oriented in a non-parallel direction relative to the airflow through the housing.

The aerosol delivery device can be configured such that the variable signal output by the sensor varies based on airflow rate. Further, the at least one functional element controlled based upon the variable signal from the sensor can be selected from the group consisting of a heating member, a fluid delivery member, a sensory feedback member, and combinations thereof.

In further embodiments, the present disclosure also can provide methods for controlling operation of an aerosol delivery device. In some embodiments, a method can comprise: detecting one or more properties of an airflow through the aerosol delivery device; outputting a variable signal that varies based upon the one or more properties of the airflow; and controlling the operation of at least one functional element of the aerosol delivery device based upon the variable output signal.

The detecting of the one or more properties of the airflow through the aerosol delivery device can comprise detecting movement of a portion of a sensor. In particular, the detecting can relate to detecting angular displacement of an extension of the sensor or a change in bend radius of the extension.

The method particularly can comprise one or more of controlling the operation of a heating member of the aerosol delivery device, controlling the operation of a fluid delivery member of the aerosol delivery device, and controlling the operation of a sensory feedback member of the aerosol delivery device. In some embodiments, the method can comprise controlling at least one property of the electrical current supplied to the heating member. In particular, the method can comprise supplying the electrical current to the heating member proportionally to a rate of the airflow detected. In other embodiments, the method can comprise controlling the supply rate of an aerosol precursor composition from a reservoir to an atomizer. In particular, the method can comprise supplying the aerosol precursor composition to the atomizer proportionally to a rate of the airflow detected. In further embodiments, the method can comprise controlling a lighting configuration of a lighting element. In particular, the method can comprise changing at least one of a color, a lighting pattern, a lighting duration, and an intensity of the lighting element based on a rate of the airflow detected.

BRIEF DESCRIPTION OF THE FIGURES

Figure 1:
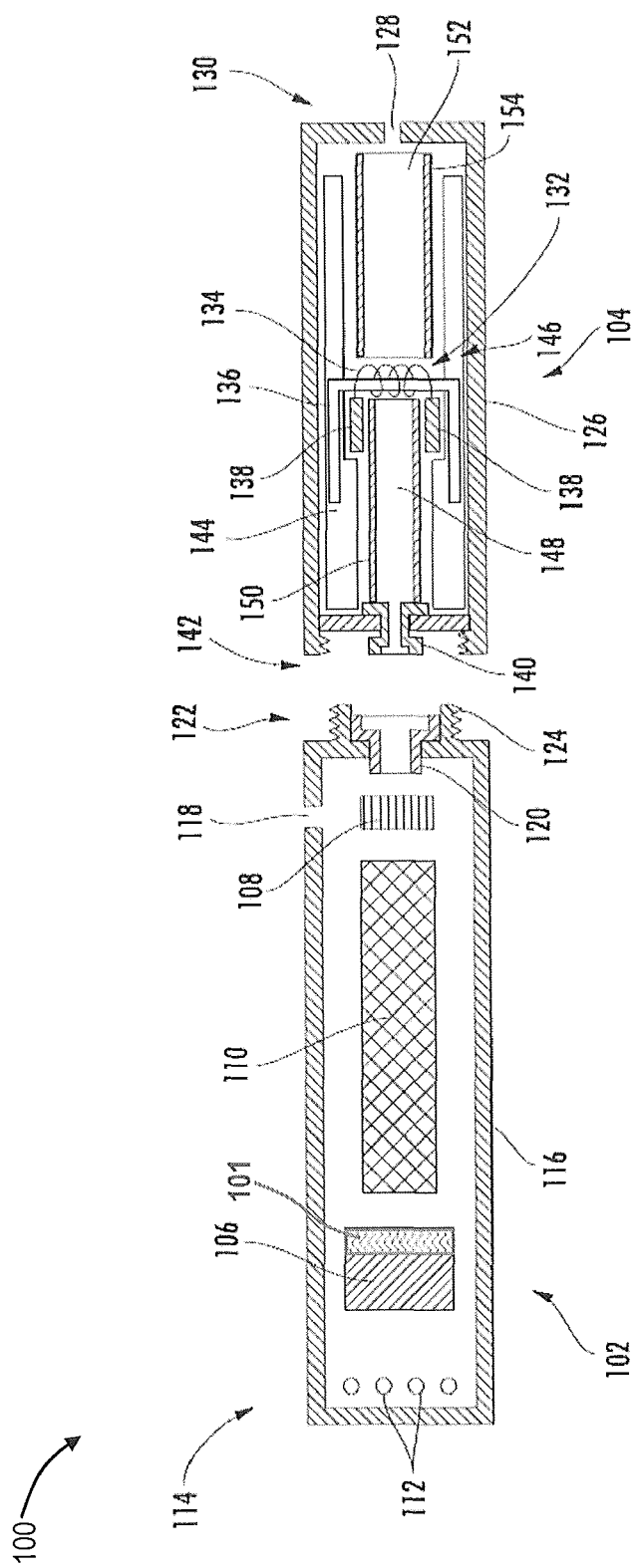
Figure 2:
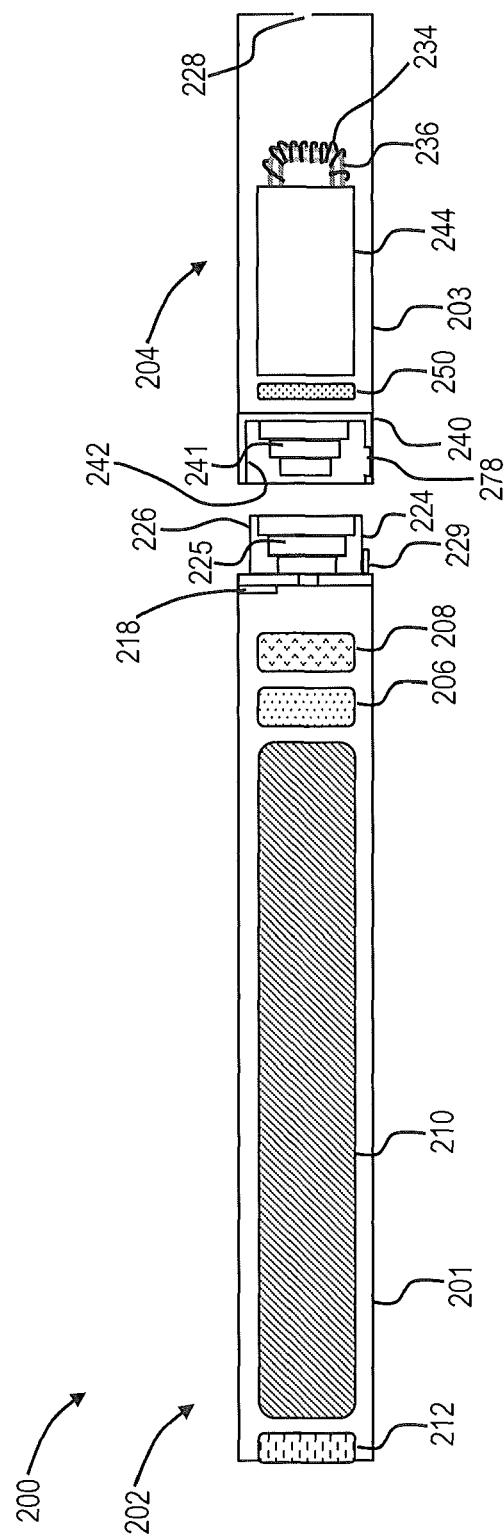
Figure 3:
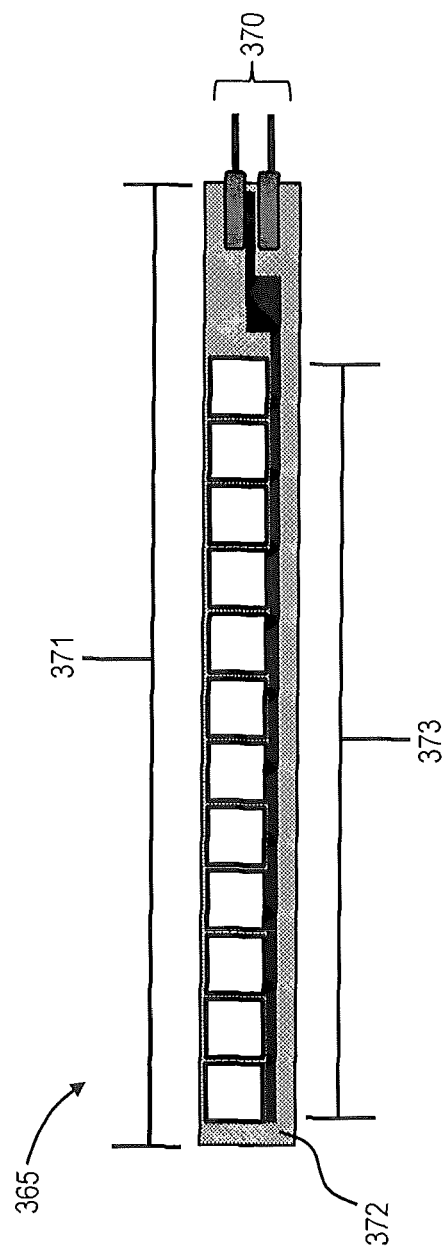
Figure 5:
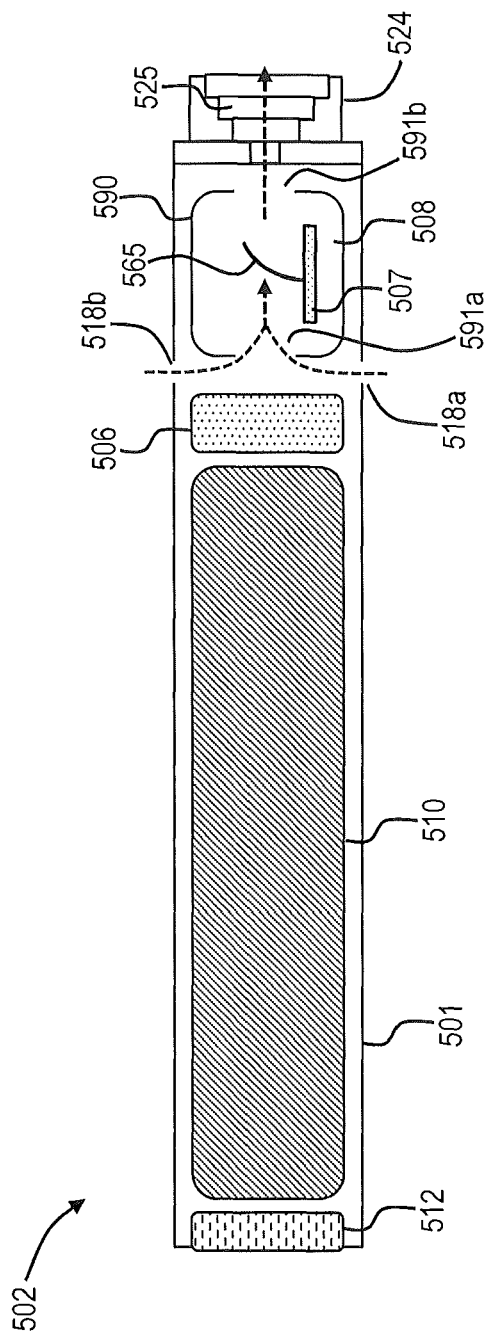
Figure 6:
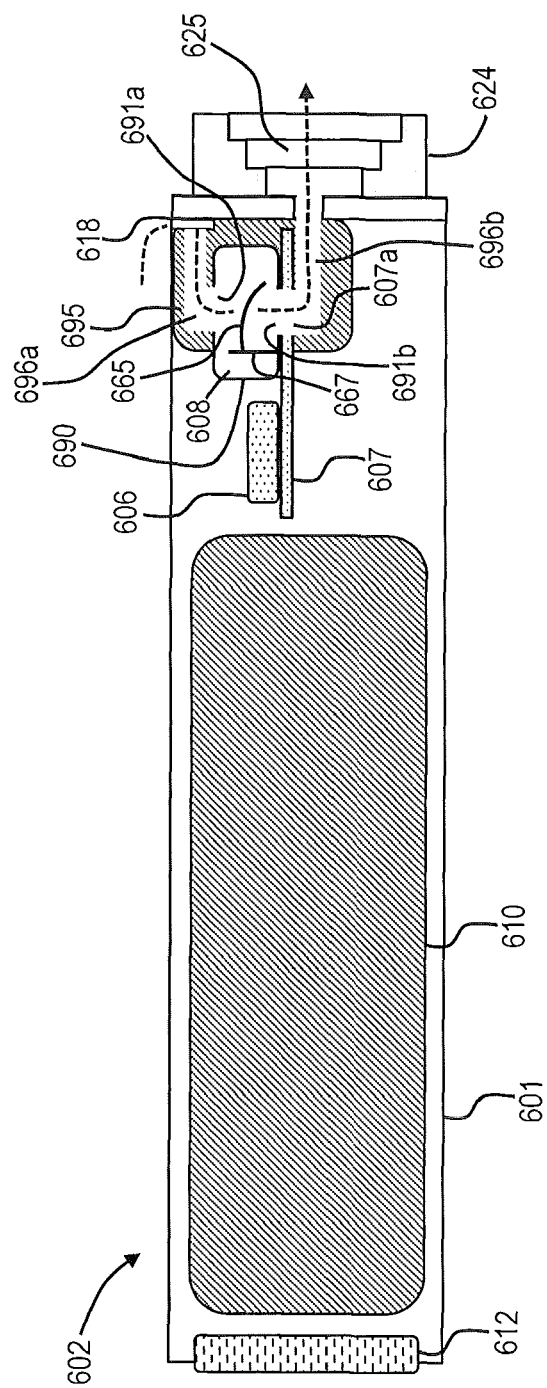
Figure 7:
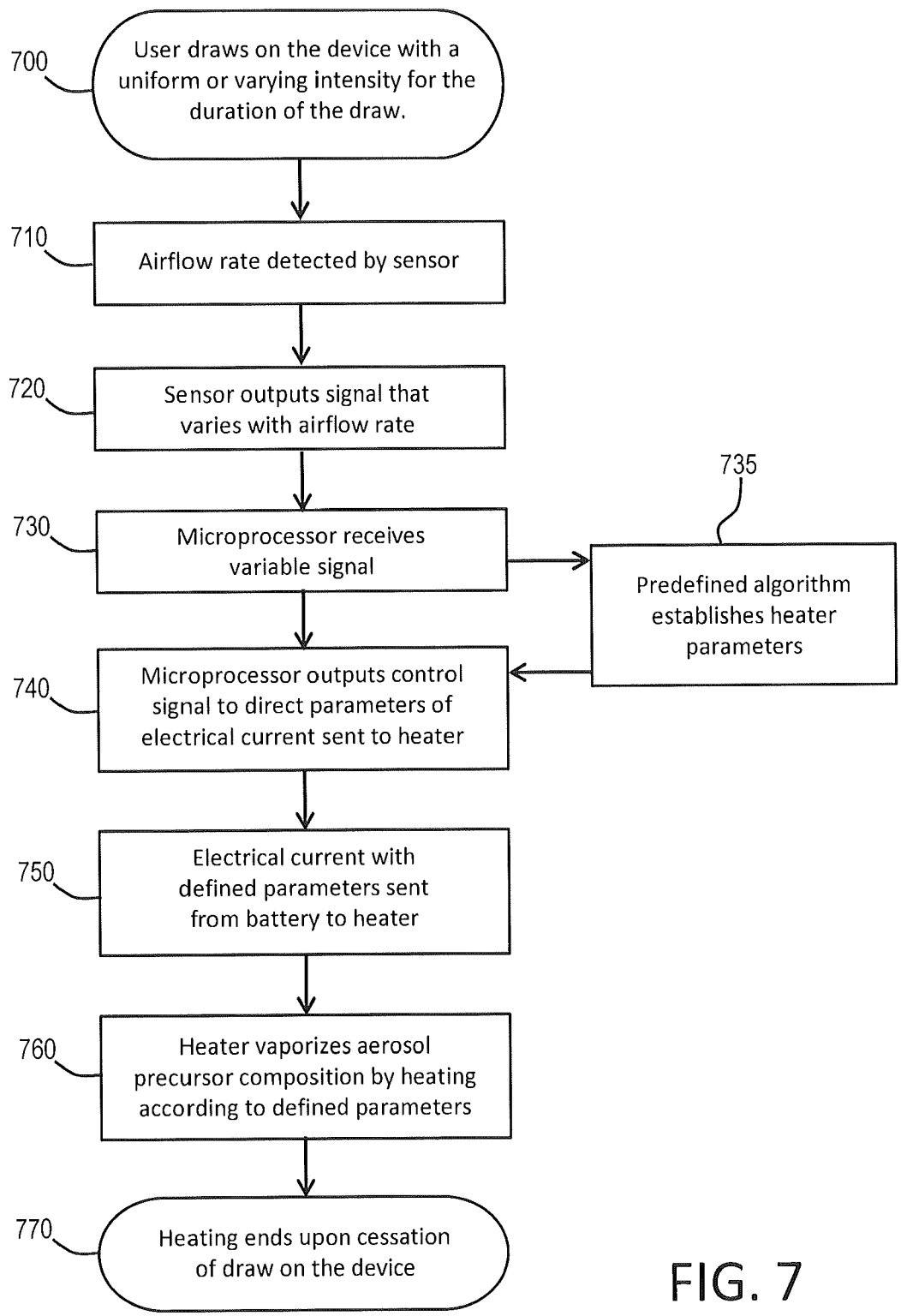

Having thus described the disclosure in the foregoing general terms, reference will now be made to the accompanying drawings, which are not necessarily drawn to scale, and wherein:

FIG. 1 is a sectional view through an aerosol delivery device according to an example embodiment of the present disclosure comprising a control body and a cartridge;

FIG. 2 is a sectional view through an aerosol delivery device comprising a cartridge and a control body according to an example embodiment of the present disclosure;

FIG. 3 is a front view of a flex/bend sensor for use in an aerosol delivery device according to the present disclosure, the sensor being configured for variable signal output relative to flexing or bending of an extension;

FIGS. 4a through 4d are partial cross-sections through an aerosol delivery device according to the present disclosure, the figures showing flexing or bending of a flex/bend sensor relative to airflow through the device;

FIG. 5 is a sectional view through a control body including a flow sensor element comprising a flex/bend sensor according to an embodiment of the present disclosure;

FIG. 6 is a sectional view through a control body including a flow sensor element comprising a flex/bend sensor according to another embodiment of the present disclosure; and FIG. 7 is a flow chart illustrating operations of an aerosol delivery device according to the present disclosure allowing for real-time changes in heater control based on manual input by a user, particularly based on draw on the device by a user.

DETAILED DESCRIPTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure provides descriptions of aerosol delivery devices or smoking articles, such as so-called "e-cigarettes." It should be understood that the mechanisms, components, features, and methods may be embodied in many different forms and associated with a variety of articles.

In this regard, the present disclosure provides descriptions of aerosol delivery devices that use electrical energy to heat a material (preferably without combusting or pyrolyzing the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion or pyrolysis of any component of that article or device. The aerosol delivery device may not produce smoke in the sense of the aerosol resulting from by-products of combustion or pyrolysis of tobacco, but rather, that the article or device may yield vapors (including vapors within aerosols that can be considered to be visible aerosols that might be considered to be described as smoke-like) resulting from volatilization or vaporization of certain components of the article or device. In highly preferred embodiments, aerosol delivery devices may incorporate tobacco and/or components derived from tobacco.

Aerosol delivery devices of the present disclosure also can be characterized as being vapor-producing articles, smoking articles, or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar, or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing, or the elongated housing can be formed of two or more separable bodies. For example, an aerosol delivery device can comprise an elongated shell or body that can be substantially tubular in shape and, as such, resemble the shape of a conventional cigarette or cigar. In one embodiment, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., a rechargeable battery and various electronics for controlling the operation of that article), and at the other end and removably attached thereto an outer body or shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various aerosol delivery device designs and component arrangements can be appreciated upon consideration of the commercially available electronic aerosol delivery devices, such as those representative products listed in the background art section of the present disclosure. An aerosol delivery device with multiple outer bodies comprising components useful according to the present disclosure is described in U.S. application Ser. No. 14/170,838 to Bless et al., filed Feb. 3, 2014, which is incorporated herein by reference in its entirety.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller or microprocessor), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw). Exemplary formulations for aerosol precursor materials that may be used according to the present disclosure are described in U.S. Pat. Pub. No. 2013/0008457 to Zheng et al., U.S. Pat. Pub. No. 2013/0213417 to Chong et al., and U.S. Pat. Pub. No. 2014/0000638 to Sebastian et al., the disclosures of which are incorporated herein by reference in their entirety.

Alignment of the components within the aerosol delivery device can vary. In specific embodiments, the aerosol precursor composition can be located near an end of the article (e.g., within a cartridge, which in certain circumstances can be replaceable and disposable), which may be proximal to the mouth of a user so as to maximize aerosol delivery to the user. Other configurations, however, are not excluded. Generally, the heating member can be positioned sufficiently near the aerosol precursor composition so that heat from the heating member can volatilize the aerosol precursor (as well as one or more flavorants, medicaments, or the like that may likewise be provided for delivery to a user) and form an aerosol for delivery to the user. When the heating member heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various aerosol delivery device components can be appreciated upon consideration of the commercially available electronic aerosol delivery devices.

An aerosol delivery device incorporates a battery or other electrical power source to provide electrical current flow sufficient to provide various functionalities to the article, such as heating by the heating member, powering of control systems, powering of indicators, and the like. The power source can take on various embodiments. Preferably, the power source is configured to deliver sufficient power to rapidly heat the heating member to provide for aerosol formation and power the article through use for the desired duration of time. The power source preferably is sized to fit conveniently within the aerosol delivery device so that the aerosol delivery device can be easily handled; and additionally, a preferred power source is of a sufficiently light weight to not detract from a desirable smoking experience.

One example embodiment of an aerosol delivery device 100 is provided in FIG. 1. As seen in the cross-section illustrated therein, the aerosol delivery device 100 can comprise a control body 102 and a cartridge 104 that can be permanently or detachably aligned in a functioning relationship. Although a threaded engagement is illustrated in FIG. 1, it is understood that further means of engagement may be employed, such as a press-fit engagement, interference fit, a magnetic engagement, or the like. In particular, connection components, such as further described herein may be used. For example, the control body may include a coupler that is adapted to engage a connector on the cartridge.

In specific embodiments, one or both of the control body 102 and the cartridge 104 may be referred to as being disposable or as being reusable. For example, the control body may have a replaceable battery or a rechargeable battery and thus may be combined with any type of recharging technology, including connection to a typical electrical outlet, connection to a car charger (i.e., cigarette lighter receptacle), and connection to a computer, such as through a universal serial bus (USB) cable. For example, an adaptor including a USB connector at one end and a control body connector at an opposing end is disclosed in U.S. patent application Ser. No. 13/840,264 to Novak et al., filed Mar. 15, 2013, which is incorporated herein by reference in its entirety. Further, in some embodiments the cartridge may comprise a single-use cartridge, as disclosed in U.S. patent application Ser. No. 13/603,612 to Chang et al., filed Sep. 5, 2012, which is incorporated herein by reference in its entirety.

In the exemplified embodiment, the control body 102 includes a control component 106 (e.g., a microcontroller), a sensor 108, and a battery 110, which can be variably aligned, and can include a plurality of indicators 112 at a distal end 114 of an outer housing 116. The indicators 112 can be provided in varying numbers and can take on different shapes and can even be an opening in the body (such as for release of sound when such indicators are present). In the exemplified embodiment, a haptic feedback component 101 is included with the control component 106. As such, the haptic feedback component may be integrated with one or more components of a smoking article for providing vibration or like tactile indication of use or status to a user. See, for example, the disclosure of U.S. patent application Ser. No. 13/946,309 to Galloway et al., filed Jul. 19, 2013, which is incorporated herein by reference in its entirety.

An air intake 118 may be positioned in the outer housing 116 of the control body 102. A coupler 120 also is included at the proximal attachment end 122 of the control body 102 and may extend into a control body projection 124 to allow for ease of electrical connection with an atomizer or a component thereof, such as a resistive heating element (described below) when the cartridge 104 is attached to the control body. Although the air intake 118 is illustrated as being provided in the outer housing 116, in another embodiment the air intake may be provided in a coupler as described, for example, in U.S. patent application Ser. No. 13/841,233 to DePiano et al., filed Mar. 15, 2013 or U.S. patent application Ser. No. 14/193,961 to Worm et al., filed Feb. 28, 2014, which are incorporated herein by reference in their entireties.

The cartridge 104 includes an outer housing 126 with a mouth opening 128 at a mouthend 130 thereof to allow passage of air and entrained vapor (i.e., the components of the aerosol precursor composition in an inhalable form) from the cartridge to a consumer during draw on the aerosol delivery device 100. The aerosol delivery device 100 may be substantially rod-like or substantially tubular shaped or substantially cylindrically shaped in some embodiments. In other embodiments, further shapes and dimensions are encompassed—e.g., a rectangular or triangular cross-section, or the like.

The cartridge 104 further includes an atomizer 132 comprising a resistive heating element 134 (e.g., a wire coil) configured to produce heat and a liquid transport element 136 (e.g., a wick) configured to transport a liquid. Various embodiments of materials configured to produce heat when electrical current is applied therethrough may be employed to form the resistive heating element 134. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), and ceramic (e.g., a positive temperature coefficient ceramic).

Electrically conductive heater terminals 138 (e.g., positive and negative terminals) at the opposing ends of the heating element 134 are configured to direct current flow through the heating element and configured for attachment to the appropriate wiring or circuit (not illustrated) to form an electrical connection of the heating element with the battery 110 when the cartridge 104 is connected to the control body 102. Specifically, a plug 140 may be positioned at a distal attachment end 142 of the cartridge 104. When the cartridge 104 is connected to the control body 102, the plug 140 engages the coupler 120 to form an electrical connection such that current controllably flows from the battery 110, through the coupler and plug, and to the heating element 134. The outer housing 126 of the cartridge 104 can continue across the distal attachment end 142 such that this end of the cartridge is substantially closed with the plug 140 protruding therefrom.

A liquid transport element can be combined with a reservoir to transport an aerosol precursor composition to an aerosolization zone. In the embodiment shown in FIG. 1, the cartridge 104 includes a reservoir layer 144 comprising layers of nonwoven fibers formed into the shape of a tube encircling the interior of the outer housing 126 of the cartridge, in this embodiment. An aerosol precursor composition is retained in the reservoir layer 144. Liquid components, for example, can be sorptively retained by the reservoir layer 144. The reservoir layer 144 is in fluid connection with a liquid transport element 136. The liquid transport element 136 transports the aerosol precursor composition stored in the reservoir layer 144 via capillary action to an aerosolization zone 146 of the cartridge 104. As illustrated, the liquid transport element 136 is in direct contact with the heating element 134 that is in the form of a metal wire coil in this embodiment.

It is understood that an aerosol delivery device that can be manufactured according to the present disclosure can encompass a variety of combinations of components useful in forming an electronic aerosol delivery device. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety. Further, U.S. patent application Ser. No. 13/602,871 to Collett et al., filed Sep. 4, 2012, discloses an electronic smoking article including a microheater, and which is incorporated herein by reference in its entirety.

In certain embodiments according to the present disclosure, a heater may comprise a metal wire, which may be wound with a varying pitch around a liquid transport element, such as a wick. An exemplary variable pitch heater that may be used according to the present disclosure is described in U.S. patent application Ser. No. 13/827,994 to DePiano et al., filed Mar. 14, 2013, the disclosure of which is incorporated herein by reference in its entirety.

In certain embodiments according to the present disclosure, a reservoir may particularly be formed of a fibrous material, such as a fibrous mat or tube that may absorb or adsorb a liquid material. For example, a cellulose acetate material can be used.

In another embodiment substantially the entirety of the cartridge may be formed from one or more carbon materials, which may provide advantages in terms of biodegradability and absence of wires. In this regard, the heating element may comprise a carbon foam, the reservoir may comprise carbonized fabric, and graphite may be employed to form an electrical connection with the battery and controller. Such carbon cartridge may be combined with one or more elements as described herein for providing illumination of the cartridge in some embodiments. Example embodiments of carbon-based cartridges are provided in U.S. Pat. Pub. No. 2013/0255702 to Griffith Jr. et al. and U.S. patent application Ser. No. 14/011,192 to Davis et al., filed Aug. 28, 2013, which are incorporated herein by reference in their entirety.

In use, when a user draws on the article 100, airflow is detected by the sensor 108, the heating element 134 is activated, and the components for the aerosol precursor composition are vaporized in the aerosolization zone 146. Drawing upon the mouthend 130 of the article 100 causes ambient air to enter the air intake 118 and pass through the central opening in the coupler 120 and the central opening in the plug 140. In the cartridge 104, the drawn air passes through an air passage 148 in an air passage tube 150 and combines with the formed vapor in the aerosolization zone 146 to form an aerosol. The aerosol is whisked away from the aerosolization zone 146, passes through an air passage 152 in an air passage tube 154, and out the mouth opening 128 in the mouthend 130 of the article 100.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., the disclosure of which is incorporated herein by reference in its entirety.

An exemplary mechanism that can provide puff-actuation capability includes a Model 163PC01D36 silicon sensor, manufactured by the MicroSwitch division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Further description of current regulating circuits and other control components, including microcontrollers that can be useful in the present aerosol delivery device, are provided in U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., and U.S. Pat. No. 7,040,314 to Nguyen et al., all of which are incorporated herein by reference in their entireties. Such devices may be utilized in combination with or in addition to a variable output sensor as described herein. For example, a sensor as referenced above may be utilized to activate one or more functions of an aerosol delivery device, and a variable output sensor as described herein may be utilized to activate one or more different functions of the aerosol delivery device.

Reference also is made to International Publications WO 2013/098396 to Talon, WO 2013/098397 to Talon, and WO 2013/098398 to Talon, which describe controllers configured to control power supplied to a heater element from a power source as a means to monitor a status of the device, such as heater temperature, air flow past a heater, and presence of an aerosol forming material near a heater. In particular embodiments, the present disclosure provides a variety of control systems adapted to monitor status indicators, such as through communication of a microcontroller in a control body and a microcontroller or other electronic component in a cartridge component.

The aerosol precursor, or vapor precursor composition, can vary. Most preferably, the aerosol precursor is composed of a combination or mixture of various ingredients or components. The selection of the particular aerosol precursor components, and the relative amounts of those components used, may be altered in order to control the overall chemical composition of the mainstream aerosol produced by the aerosol generating piece. Of particular interest are aerosol precursors that can be characterized as being generally liquid in nature. For example, representative generally liquid aerosol precursors may have the form of liquid solutions, viscous gels, mixtures of miscible components, or liquids incorporating suspended or dispersed components. Typical aerosol precursors are capable of being vaporized upon exposure to heat under those conditions that are experienced during use of the aerosol generating pieces that are characteristic of the current disclosure; and hence are capable of yielding vapors and aerosols that are capable of being inhaled.

For aerosol delivery systems that are characterized as electronic cigarettes, the aerosol precursor most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor may incorporate a so-called "aerosol forming materials." Such materials have the ability to yield visible aerosols when vaporized upon exposure to heat under those conditions experienced during normal use of aerosol generating pieces that are characteristic of the current disclosure. Such aerosol forming materials include various polyols or polyhydric alcohols (e.g., glycerin, propylene glycol, and mixtures thereof). Many embodiments of the present disclosure incorporate aerosol precursor components that can be characterized as water, moisture or aqueous liquid. During conditions of normal use of certain aerosol generating pieces, the water incorporated within those pieces can vaporize to yield a component of the generated aerosol. As such, for purposes of the current disclosure, water that is present within the aerosol precursor may be considered to be an aerosol forming material.

It is possible to employ a wide variety of optional flavoring agents or materials that alter the sensory character or nature of the drawn mainstream aerosol generated by the aerosol delivery system of the present disclosure. For example, such optional flavoring agents may be used within the aerosol precursor to alter the flavor, aroma and organoleptic properties of the aerosol. Certain flavoring agents may be provided from sources other than tobacco. Exemplary flavoring agents may be natural or artificial in nature, and may be employed as concentrates or flavor packages.

Exemplary flavoring agents include vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar and pipe tobaccos. Syrups, such as high fructose corn syrup, also can be employed. Certain flavoring agents may be incorporated within aerosol forming materials prior to formulation of a final aerosol precursor mixture (e.g., certain water soluble flavoring agents can be incorporated within water, menthol can be incorporated within propylene glycol, and certain complex flavor packages can be incorporated within propylene glycol).

Aerosol precursors also may include ingredients that exhibit acidic or basic characteristics (e.g., organic acids, ammonium salts or organic amines). For example, certain organic acids (e.g., levulinic acid, succinic acid, lactic acid, and pyruvic acid) may be included in an aerosol precursor formulation incorporating nicotine, preferably in amounts up to being equimolar (based on total organic acid content) with the nicotine. For example, the aerosol precursor may include about 0.1 to about 0.5 moles of levulinic acid per one mole of nicotine, about 0.1 to about 0.5 moles of succinic acid per one mole of nicotine, about 0.1 to about 0.5 moles of lactic acid per one mole of nicotine, about 0.1 to about 0.5 moles of pyruvic acid per one mole of nicotine, or various permutations and combinations thereof, up to a concentration wherein the total amount of organic acid present is equimolar to the total amount of nicotine present in the aerosol precursor.

As one non-limiting example, a representative aerosol precursor can have the form of a mixture of about 70% to about 90% glycerin, often about 75% to about 85% glycerin; about 5% to about 20% water, often about 10% to about 15% water; about 1% to about 10% propylene glycol, often about 4% to about 8% propylene glycol; about 0.1% to about 6% nicotine, often about 1.5% to about 5% nicotine; and optional flavoring agent in an amount of up to about 6%, often about 0.1% to about 5% flavoring agent; on a weight basis. For example, a representative aerosol precursor may have the form of a formulation incorporating greater than about 76% glycerin, about 14% water, about 7% propylene glycol, about 1% to about 2% nicotine, and less than about 1% optional flavoring agent, on a weight basis. For example, a representative aerosol precursor may have the form of a formulation incorporating greater than about 75% glycerin, about 14% water, about 7% propylene glycol, about 2.5% nicotine, and less than about 1% optional flavoring agent. For example, a representative aerosol precursor may have the form of a formulation incorporating greater than about 75% glycerin, about 5% water, about 8% propylene glycol, about 6% nicotine, and less than about 6% optional flavoring agent, on a weight basis.

As another non-limiting example, a representative aerosol precursor can have the form of a mixture of about 40% to about 70% glycerin, often about 50% to about 65% glycerin; about 5% to about 20% water, often about 10% to about 15% water; about 20% to about 50% propylene glycol, often about 25% to about 45% propylene glycol; about 0.1% to about 6% nicotine, often about 1.5% to about 5% nicotine; about 0.5% to about 3%, often about 1.5% to about 2% menthol; and optional additional flavoring agent in an amount of up to about 6%, often about 0.1% to about 5% flavoring agent; on a weight basis. For example, a representative aerosol precursor may have the form of a formulation incorporating about 50% glycerin, about 11% water, about 28% propylene glycol, about 5% nicotine, about 2% menthol, and about 4% other flavoring agent, on a weight basis.

Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al. and 2014/0060554 to Collett et al., the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. Typically, the amount of aerosol precursor incorporated within the aerosol delivery system, and particularly within the aerosol generating piece, is less than about 2 g, generally less than about 1.5 g, often less than about 1 g and frequently less than about 0.5 g.

Additional representative types of components that yield visual cues or indicators, such as light emitting diode (LED) components, and the configurations and uses thereof, are described in U.S. Pat. Nos. 5,154,192 to Sprinkel et al.; U.S. Pat. No. 8,499,766 to Newton and U.S. Pat. No. 8,539,959 to Scatterday; and U.S. patent application Ser. No. 14/173,266, filed Feb. 5, 2014, to Sears et al.; which are incorporated herein by reference.

Yet other features, controls or components that can be incorporated into aerosol delivery systems of the present disclosure are described in U.S. Pat. Nos. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. Nos. 2010/0163063 by Fernando et al.; 2013/0192623 to Tucker et al.; 2013/0298905 to Leven et al.; 2013/0180553 to Kim et al. and 2014/0000638 to Sebastian et al.; and U.S. patent application Ser. Nos. 13/840,264, filed Mar. 15, 2013, to Novak et al. and Ser. No. 13/841,233, filed Mar. 15, 2013, to DePiano et al.; which are incorporated herein by reference.

The foregoing description of use of the article can be applied to the various embodiments described herein through minor modifications, which can be apparent to the person of skill in the art in light of the further disclosure provided herein. The above description of use, however, is not intended to limit the use of the article but is provided to comply with all necessary requirements of disclosure of the present disclosure.

Any of the elements shown in the article illustrated in FIG. 1 or as otherwise described above may be included in an aerosol delivery device according to the present disclosure. In particular, any of the above described and illustrated components of a control body can be incorporated into a control body according to the present disclosure. Likewise, any of the above described and illustrated components of a cartridge can be incorporated into a cartridge that can be combined with a control body according to the present disclosure.

An exemplary embodiment of a smoking article 200 according to the present disclosure is shown in FIG. 2. As illustrated therein, a control body 202 can be formed of a control body shell 201 that can include a control component 206, a flow sensor 208, a battery 210, and an LED 212. A cartridge 204 can be formed of a cartridge shell 203 enclosing the reservoir 244 that is in fluid communication with a liquid transport element 236 adapted to wick or otherwise transport an aerosol precursor composition stored in the reservoir housing to a heater 234. An opening 228 may be present in the cartridge shell 203 to allow for egress of formed aerosol from the cartridge 204. Such components are representative of the components that may be present in a cartridge and are not intended to limit the scope of cartridge components that are encompassed by the present disclosure.

Although the control component 206 and the flow sensor 208 are illustrated separately, it is understood that the control component and the flow sensor may be combined as an electronic circuit board with the air flow sensor attached directly thereto. Further, the electronic circuit board may be positioned horizontally relative the illustration of FIG. 2 in that the electronic circuit board can be lengthwise parallel to the central axis of the control body. In some embodiments, the air flow sensor may comprise its own circuit board or other base element to which it can be attached.

The cartridge 204 also may include one or more electronic components 250, which may include an integrated circuit, a memory component, a sensor, or the like. The electronic component 250 may be adapted to communicate with the control component 206.

The control body 202 and the cartridge 204 may include components adapted to facilitate a fluid engagement therebetween. As illustrated in FIG. 2, the control body 202 can include a coupler 224 having a cavity 225 therein. The cartridge 204 can include a base 240 adapted to engage the coupler 224 and can include a projection 241 adapted to fit within the cavity 225. Such engagement can facilitate a stable connection between the control body 202 and the cartridge 204 as well as establish an electrical connection between the battery 210 and control component 206 in the control body and the heater 234 in the cartridge. Further, the control body shell 201 can include an air intake 218, which may be a notch in the shell where it connects to the coupler 224 that allows for passage of ambient air around the coupler and into the shell where it then passes through the cavity 225 of the coupler and into the cartridge through the projection 241.

A coupler and a base useful according to the present disclosure are described in U.S. patent application Ser. No. 13/840,264 to Novak et al., filed Mar. 15, 2013, the disclosure of which is incorporated herein by reference in its entirety. For example, a coupler as seen in FIG. 2 may define an outer periphery 226 configured to mate with an inner periphery 242 of the base 240. In one embodiment the inner periphery of the base may define a radius that is substantially equal to, or slightly greater than, a radius of the outer periphery of the coupler. Further, the coupler 224 may define one or more protrusions 229 at the outer periphery 226 configured to engage one or more recesses 278 defined at the inner periphery of the base. However, various other embodiments of structures, shapes, and components may be employed to couple the base to the coupler. In some embodiments the connection between the base 240 of the cartridge 204 and the coupler 224 of the control body 202 may be substantially permanent, whereas in other embodiments the connection therebetween may be releasable such that, for example, the control body may be reused with one or more additional cartridges that may be disposable and/or refillable.

In some embodiments, a sensor for use in an aerosol delivery device according to the present disclosure may be configured to detect an airflow through at least a portion of a housing (e.g., a control body housing, a cartridge housing, or a single housing comprising control components and cartridge components). In response to a detected airflow, the sensor can be configured to output a variable signal, which can vary, for example, based upon one or more properties of the airflow. Such variable output sensor may be utilized in a variety of embodiments of aerosol delivery devices as described below. Moreover, the sensor 108 in FIG. 1 and/or the sensor 208 in FIG. 2 may be a variable output sensor as described herein.

A sensor adapted to detect an airflow and output a variable signal can be distinguished from a sensor that functions essentially as an on/off switch. Such on/off sensors typically are configured to generate an electrical current in response to a pressure differential, and the induced current provides a signal to a controller to initiate power flow from a battery to a heater. The absence of the induced electrical current indicates an "off" state, and the presence of the induced current provides an "on" signal. The "on" signal has no variance and specifically does not vary based upon the nature of the airflow. Thus, sensors in known aerosol delivery devices are not configured to provide a variable signal, only a static signal.

A sensor for use according to the present disclosure can comprise any sensor adapted to provide a variable signal as described herein. For example, in some embodiments, piezo elements, strain gauges, flex/bend sensors, or other analog measurement devices may be used.

A sensor configured to provide a variable signal is further described herein in relation to a flex/bend sensor. Such description is provided for ease of understanding of the disclosed subject matter and should not be construed as limiting of the disclosure. Similar sensors configured to provide a variable signal, such as relative to airflow rate, can also be used.

In some embodiments, a flex/bend sensor can comprise any sensor comprising at least one element configured to flex or bend when an air flow is applied to the element. The flexing or bending of the element particularly can increase as the rate of airflow increases.

An exemplary flex/bend sensor useful according to the present disclosure is shown in FIG. 3. As seen therein, a sensor 365 comprises an electrical connection 370 and an extension 371. The extension 371 can have a variety of dimensions and is preferentially sized for positioning within a housing or shell (see element 201 in FIG. 2, for example). For example, the extension can have a length of less than about 10 mm, less than about 8 mm, or less than about 6 mm (e.g., about 3 mm to about 8 mm, about 3.5 mm to about 7 mm, or about 4 mm to about 6 mm). The extension can have a width of about 0.5 mm to about 5 mm, about 1 mm to about 4 mm, or about 1.5 mm to about 3.5 mm and a thickness of about 0.1 mm to about 2 mm, about 0.2 mm to about 1.5 mm, or about 0.25 mm to about 1 mm. The extension can be substantially elongate and thus may have a length that is greater than the width of the extension and greater than the thickness of the extension.

The extension 371 can comprise a substrate 372 that can be formed of any flexible or bendable material, such as polymeric materials. For example, the substrate 372 can comprise a polyester (e.g., polyethylene terephthalate) or any similar material configured to bend or flex in response to an applied force (e.g., airflow) and return to a non-bent or non-flexed state upon removal of the applied force.

The extension 371 of the sensor 365 further can comprise an electrically conductive array 373 in physical connection with the substrate 371. The electrically conductive array 373 that can be configured to exhibit a change in one or more electrical properties thereof in response to bending or flexing of the substrate 372. For example, the array 373 may be configured for undergoing a change in one or more of electrical resistance, resistivity, conductance, or conductivity. Non-limiting examples of electrically conductive arrays include conductive elastomers, conductive inks, conductive fluids, slide resistors, force resistors, and the like. See, for example, the materials described in U.S. Pat. No. 5,086,705 to Gentile et al. and U.S. Pat. No. 5,411,789 to Margolin, the disclosures of which are incorporated herein by reference in their entireties.

The electrically conductive array 373 may be layered on or embedded in the substrate 372. For example, the array may be printed on the substrate. In some embodiments, a further layer may be provided over the electrically conductive array 373 on the substrate 372 such that the array may be sandwiched between two layers.

The electrically conductive array can comprise copper, carbon, or other electrically conductive materials adapted for measuring resistance therethrough. For example, a copper circuit can be printed onto the surface of an extension substrate. As another example, carbon resistive element can be embedded or otherwise attached to the extension substrate. In some embodiments, a resistive material can be sandwiched between metal foil layers (e.g., copper). This layered element can be surrounded by a polymeric covering, such as a heat shrinkable tubing. The resistive output of the sensor can change relative to the bend radius of the extension. The flex/bend sensor can be uni-directional or bi-directional.

In use, the flex/bend sensor can be arranged within a device such that when air flows across the sensor, the extension can flex or bend. The flexure or bending can be defined in relation to an angular displacement of the substrate in response to the applied force. The signal output by the flex/bend sensor can vary based upon the degree of flexing or bending of the extension. In some embodiments, the variable signal output by the sensor can correspond to an angular displacement of the extension, particularly an angular displacement of the extension substrate. This is illustrated in FIGS. 4a through 4d, which illustrated partial cross-sectional views of exemplary aerosol delivery devices. Although not illustrated in FIG. 4 for simplicity, it is understood that the electronic circuit board can be in electrical connection with one or more additional elements of the aerosol delivery device, such as a battery, a controller, and/or heater, for example. The combination of the variable output sensor with various further elements of the aerosol delivery device is shown, for example, in FIG. 5 and FIG. 6. Moreover, the electronic circuit board illustrated in FIG. 4a through FIG. 4d may comprise elements in addition to the variable output sensor, such as a controller, an LED, and the like.

Figure 4B:
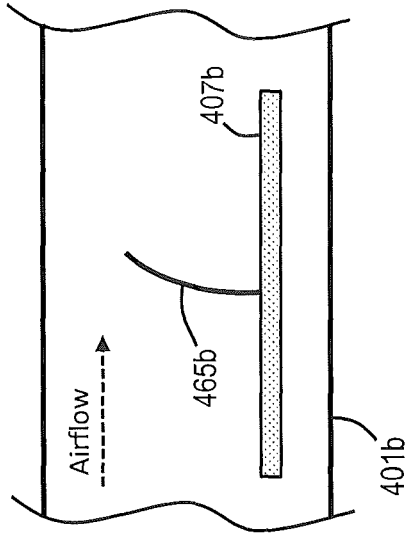
Figure 4D:
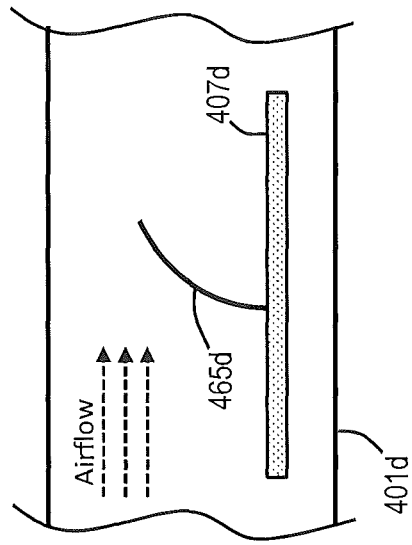
Figure 4A:
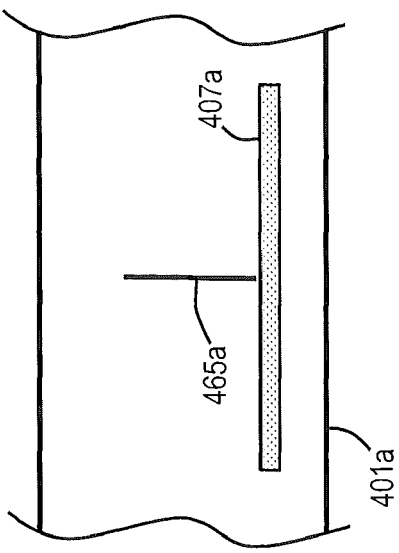

As seen in FIG. 4a, a flex/bend sensor 465a is positioned within a housing 401a and is in connection with an electronic circuit board 407a. The electronic circuit board 407a in this embodiment is substantially parallel with the longitudinal axis of the housing 401a. In FIG. 4a, no airflow is passing through the housing 401a, and the sensor 465a is at a resting position which, in this embodiment, is substantially perpendicular to the longitudinal axis of the housing.

In FIG. 4b, an airflow has been established through the housing 401b. The airflow is of a magnitude such that the flex/bend sensor 465b flexes or bends in the same direction as the airflow while the electronic circuit board 407b remains substantially unmoved by the airflow.

Figure 4C:
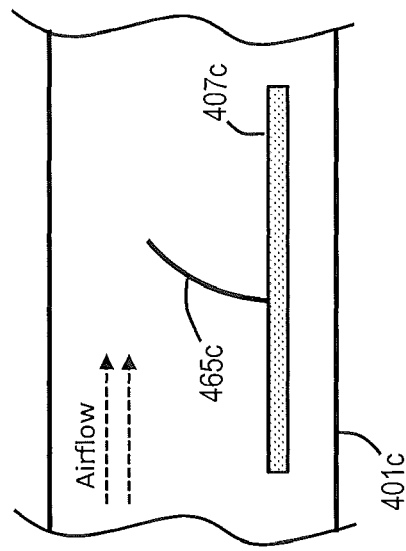

In FIG. 4c, the airflow through the housing 401c is increased in magnitude relative to the airflow in FIG. 4b. In response, the flex/bend sensor 465c flexes or bends to a greater degree in relation to the flexing or bending caused by the lesser airflow in FIG. 4b.

In FIG. 4d, the airflow through the housing 401d is increased in magnitude relative to the airflow in FIG. 4c and FIG. 4b. In response, the flex/bend sensor 465d flexes or bends to a greater degree in relation to the flexing or bending caused by the lesser airflow in FIG. 4c and FIG. 4b.

A flex/bend sensor can provide a variable output across a continuous range based upon changes in electrical properties relative to the degree of flexing or bending of the extension. As such, the sensor can be characterized as a variable analog voltage divider. For example, in sensors configured for a change in resistance across the conductive array, measured resistance changes along the continuous range as the extension flexes or bends. In particular, the sensor can identify a change in angular displacement of the extension substrate by measuring a change in electrical resistance in the conductive array—e.g., as angular displacement of the substrate increases, the electrical resistance though the conductive array increases. Resistance through the conductive array can vary across a wide range, such as about 0.11 k$\Omega$ to about 300 k$\Omega$, about 1 k$\Omega$ to about 250 k$\Omega$, or about 10 k$\Omega$ to about 200 k$\Omega$.

The flex/bend sensor can be connected to an electronic circuit board that can be arranged within the housing of an aerosol delivery device in a variety of positions. The electronic circuit board can be substantially parallel to the longitudinal axis of the housing of the aerosol delivery device. In alternate embodiments, the electronic circuit board can be substantially perpendicular to the longitudinal axis of the housing.

In some embodiments, the electronic circuit board may include one or more apertures that can be positionally aligned with the flex/bend sensor, particularly with the extension of the sensor. Such apertures can at least partially define an airflow path through at least a portion of the housing, particularly such that air flows across the extension of the flex/bend sensor in a desirable direction to facilitate flexing or bending of the extension relative to airflow through the pathway.

For example, as seen in FIG. 5, a control body 502 comprises a control body housing 501 that includes an LED 512, a battery 510, a controller 506, and a flow sensor element 508. In the illustrated embodiment, the flow sensor element 508 comprises a sensor body 590 that houses an electronic circuit board 507 with a flex/bend sensor 565 connected thereto. The flow sensor element 508 also comprises apertures 591a and 591b configured to allow for entry and exit, respectively, of airflow through the flow sensor element and across the flex/bend sensor 565. The airflow (seen as dashed lines in FIG. 5) enters the control body housing 501 through air intakes 518a and 518b, passes through the flow sensor element 508 and exits the control body 502 through the cavity 525 of the coupler 524. In some embodiments, the sensor body 590 can be absent. In such embodiments, if desired, the electronic circuit board 507 can be combined with the controller 506. For example, the controller 506 can be a microcontroller connected to the electronic circuit board 507, and the flex/bend sensor 565 can be connected to the electronic circuit board.

A further embodiment illustrated in FIG. 6 again shows a control body 602 that comprises a control body housing 601 that includes an LED 612, a battery 610, a controller 606, and a flow sensor element 608. In the illustrated embodiment, the flow sensor element 608 comprises a sensor body 690 with apertures 691a and 691b configured to allow for entry and exit, respectively, of airflow through the flow sensor element and across a flex/bend sensor 665 within the sensor body 690. The flex/bend sensor 665 can include a base 667 that can be configured for electrical connection of the flex/bend sensor to one or both of the sensor body 690 and the electronic circuit board 607. For example, the base 667 may form an electrical connection to the sensor body 690 which in turn is electrically connected to the electronic circuit board 607. Alternatively, the electrical connection of the base 667 can extend through the sensor body 690 and be configured for electrical connection with the electronic circuit board 607. The electronic circuit board 607 can include an opening 607a that can be substantially aligned with the aperture 691b in the sensor body 690 such that air passing through the sensor body also passes through the electronic circuit board.

In FIG. 6, the control body housing 601 includes an air intake 618, and this air intake can be a notch in the housing where it connects to the coupler 624 that allows for passage of ambient air around the coupler. To assist in directing airflow through the air intake 618 and into the flow sensor 608, the control body 602 can include a sealing member 695 that can include a cavity 696 (formed collectively by cavities 696a and 696b) therein. The cavity 696 in the sealing member 695 can be aligned at a first end with the air intake 618 and at a second end with the aperture 691a in the sensor body 690. The sealing member 695 preferably substantially completely surrounds the flow sensor 608 and at least a portion of the electronic circuit board 607 such that airflow (shown as dashed lines in FIG. 6) passes from outside the control body housing 601 through the air intake 618, through the cavity 696 in the sealing member 695, through the aperture 691a in the sensor body 690, across the flex/bend sensor 665, through the aperture 691b in the sensor housing, through the opening 607a in the electronic circuit board, through the cavity 696b in the sealing member, and through the cavity 625 in the coupler 624. When a cartridge is combined with the control body, the airflow exiting through the cavity 625 in the coupler 625 can pass into the cartridge.

Although the sealing member 695 is illustrated in FIG. 6, other components for defining a flow channel through at least a portion of the control body housing 601 also are encompassed. For example, one or more flow tubes can be used. In such embodiments, the control body housing can define a flow channel configured to receive airflow therethrough wherein at least a portion of the flex/bend sensor (e.g., the extension of the sensor) is positioned in the flow channel. In FIG. 6, the flow channel can be defined by the cavities 696a and 696b and the sensor body 690. Although the flex/bend sensor is illustrated as being positioned within a control body housing, it is understood that a sensor as described herein for providing a variable output can be positioned within a cartridge housing or within a single housing that comprises control and cartridge elements.

In some embodiments, the flex/bend sensor can be configured relative to the control body housing and/or the direction of airflow through the control body housing. For example, a longitudinal length of the extension of the flex/bend sensor can be oriented in a non-parallel direction relative to a longitudinal length of the housing. In other embodiments, a longitudinal length of the extension of the flex/bend sensor can be oriented in a non-parallel direction relative to the airflow through the control body housing and/or relative to a flow channel for air passing through the control body housing.

As seen in FIG. 4a through FIG. 4d, the flex/bend sensor is positioned in the airflow path and flexes or bends proportionally to the airflow through the control body housing. The magnitude of the flexing or bending of the sensor can be detected along a substantially continuous range between a resting position (no flexing or bending) and a maximally flexed or bent position. In this range, the flexing or bending of the sensor can establish an output signal that varies based upon the magnitude of the flexing or bending. In some embodiments, the variable signal output by the sensor can vary based on airflow rate. In other words, as the draw on the device increases, the rate of airflow across the flex/bend sensor increases, and the sensor flexes or bends more or less as the airflow rate increases or decreases. As such, the variable signal output from the sensor can be proportional to the airflow rate through the device.

The variable signal output from the flex/bend sensor can be used by one or more control elements of the aerosol delivery device to control the operation of the device. Such operation can encompass a variety of functional elements of the device, such as a heating member, a fluid delivery member, a sensory feedback member, and the like.

For example, the variable signal from the flex/bend sensor can be used by a microprocessor to control opening and closing of a valve between a reservoir and a heating member. As the draw on the device increases and the flexing or bending of the sensor increases, the opening of the valve can be increased to allow for a greater volume of aerosol precursor composition to pass from a reservoir to a heating member. In other embodiments where a sensory feedback member is used (e.g., a LED or a vibratory element), an increased draw on the device that increases the flexing or bending of the sensor can signal the microprocessor to cause a different lighting pattern by the LED or cause a different vibration pattern by the vibratory element.

In some embodiments, the variable signal output from the flex/bend sensor can be coupled with control electronics of the device to alter the profile of a heating element in the device, such as a heater in a cartridge. In particular, the heating profile can be caused to change in real time relative to the airflow rate caused by the magnitude of the draw on the device.

The present disclosure thus further relates to a method for controlling operation of an aerosol delivery device. Such method can comprise detecting one or more properties of an airflow through the aerosol delivery device. Such detecting step can be carried out through utilization of a sensor as described herein configured for output of a variable signal (e.g., a flex/bend sensor). For example, detecting movement of a portion of a sensor (e.g., the extension of a flex/bend sensor) can be a basis for detecting one or more properties of the airflow though the aerosol delivery device. The sensor movement can be, for example, an angular displacement of an extension of a flex/bend sensor. The sensor movement further can be, for example, movement that causes a change in the bend radius of an extension on the sensor. The method further can comprise outputting a variable signal that varies based upon the one or more properties of the airflow. In particular, the sensor can output a variable signal as otherwise described herein. The method also can comprise controlling the operation of at least one functional element of the aerosol delivery device based upon the variable output signal.

In some embodiments, the method can comprise controlling at least one property of the electrical current supplied to the heating member. In particular, the method can comprise supplying the electrical current to the heating member proportionally to a rate of the airflow detected. Such control can be achieved through implementation of one or more control algorithms utilizing program code instructions.

For example, airflow rate through an aerosol delivery device can be detected with a sensor as described herein upon draw on the device by a user, and such airflow rate can be continuously detected for the duration of the draw. The airflow sensor can output a signal that can vary based upon the airflow rate. The variable signal output from the sensor can be input by the microprocessor into the control algorithm to make the defined calculations based thereon and determine the requisite parameters for one or more properties of the electrical current supplied to the heating member relative to the output signal from the sensor. The microprocessor then directs electrical current flow to the heating member with the requisite parameters to define heater function based upon the real time airflow rate through the device. In this manner, heater function can be continuously controlled and altered as necessary relative to the airflow rate through the device. This is illustrated in the flowchart provided in FIG. 7.

At operation 700 in FIG. 7, a user initiates heating by drawing on an aerosol delivery device as described herein, and the draw by the user may be uniform for the duration of the draw or vary in intensity during the draw. At operation 710, the rate of airflow through the device is detected by a sensor as described herein. At operation 720, the sensor outputs a signal that varies with the airflow rate. At operation 730, a microprocessor receives the variable signal and initiates an algorithm (operation 735) according to predefined programming to establish the predefined heater parameters relative to the airflow rate detected by the sensor. At operation 740, the microprocessor outputs a control signal that directs the parameters of the electrical current to be sent to a heater. At operation 750, electrical current with the defined parameters is sent from a battery to the heater. At operation 760, the heater heats according to the defined parameters and thus vaporizes an aerosol precursor composition. Heating ends at operation 770 with cessation of draw on the device. It is understood that processes 710 through 760 occur repeatedly and with a predetermined frequency throughout the duration of draw on the device. In this manner, heater performance can be continuously adjusted during draw on the device. More particularly, a feedback loop is established whereby user input (e.g., the intensity of draw upon the device) can modify the heating profile of the device in real time during use of the device.

The feedback loop established through use of the variable output sensor can incorporate further feedback elements. For example, U.S. patent application Ser. No. 13/837,542 to Ampolini et al., filed Mar. 15, 2013, discloses a method comprising directing an average power from a power source to a heating device arranged to heat the aerosol precursor composition and commensurately initiate a heating time period, wherein the average power corresponds to a selected power set point associated with the power source. Such methods may be combined with the methods and devices of the present disclosure to achieve even further control schemes for an aerosol delivery device.

Similar to the above, the method of the disclosure can comprise controlling further functions of the device. For example, in some embodiments, the method can comprise controlling the supply rate of an aerosol precursor composition from a reservoir to an atomizer. In particular, the method can comprise supplying the aerosol precursor composition to the atomizer proportionally to a rate of the airflow detected. As a non-limiting example, the variable signal from the sensor can be used by the controller to control the rate at which aerosol precursor composition is output from a reservoir, such as through a valve.

In other embodiments, the method can comprise controlling a lighting configuration of a lighting element. In particular, the method can comprise changing at least one of a color, a lighting pattern, a lighting duration, and an intensity of the lighting element based on a rate of the airflow detected.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A method for controlling operation of an aerosol delivery device comprising:
   detecting one or both of an airflow rate and an airflow volume of an airflow through the aerosol delivery device using a sensor that is configured for measurement of an electrical property that varies along a continuous range based upon one or both of the airflow rate and the airflow volume;
   providing from the sensor an output that varies across a continuous range relative to the measurement of the electrical property that varies along a continuous range based upon one or both of the airflow rate and the airflow volume; and
   controlling the operation of a heating member of the aerosol delivery device based upon the output provided from the sensor, controlling the operation of a sensory feedback member of the aerosol delivery device based upon the output provided from the sensor, said sensory feedback member including a lighting element and said controlling including controlling a lighting configuration of the lighting element, and optionally controlling the operation of a fluid delivery member of the aerosol delivery device based upon the output provided from the sensor;
   wherein detecting the one or more properties of the airflow through the aerosol delivery device comprises detecting angular displacement of an extension that is substantially elongate of the sensor, the extension having a free end.

2. The method of claim 1, comprising controlling at least one property of the electrical current supplied to the heating member.

3. The method of claim 2, comprising supplying the electrical current to the heating member proportionally to one or both of the airflow rate detected and the airflow volume detected.

4. The method of claim 1, comprising controlling the supply rate of an aerosol precursor composition from a reservoir to an atomizer.

5. The method of claim 4, comprising supplying the aerosol precursor composition to the atomizer proportionally to one or both of the airflow rate detected and the airflow volume detected.

6. The method of claim 1, comprising changing at least one of a color, a lighting pattern, a lighting duration, and an intensity of the lighting element based on one or both of the airflow rate detected and the airflow volume detected.

7. The method of claim 1, wherein the aerosol delivery device includes a sealing member substantially surrounding the sensor and being configured to direct the airflow through the aerosol delivery device and across the extension of the sensor.

* * * * *